(12) United States Patent
Cho et al.

(10) Patent No.: US 11,511,072 B2
(45) Date of Patent: Nov. 29, 2022

(54) ELECTRONIC DEVICE FOR PROVIDING MEDITATION CONTENTS AND OPERATING METHOD THEREOF

(71) Applicant: SAMSUNG ELECTRONICS CO., LTD., Suwon-si (KR)

(72) Inventors: Hoon Cho, Suwon-si (KR); Hongchun Chon, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 426 days.

(21) Appl. No.: 16/692,022

(22) Filed: Nov. 22, 2019

(65) Prior Publication Data

US 2020/0164176 A1 May 28, 2020

(30) Foreign Application Priority Data

Nov. 23, 2018 (KR) .......................... 10-2018-0146333

(51) Int. Cl.
*A61M 21/02* (2006.01)
*G06F 3/16* (2006.01)
*A61M 21/00* (2006.01)

(52) U.S. Cl.
CPC ............. *A61M 21/02* (2013.01); *G06F 3/165* (2013.01); *A61M 2021/005* (2013.01);
(Continued)

(58) Field of Classification Search
CPC .......... A61M 21/02; A61M 2021/0022; A61M 2021/0027; A61M 2021/0044;
(Continued)

(56) References Cited

U.S. PATENT DOCUMENTS 7,292,561 B2 11/2007 Hyun et al.
2005/0215848 A1* 9/2005 Lorenzato ............... G04F 5/025
600/27
(Continued)

FOREIGN PATENT DOCUMENTS

KR 10-2007-0061311 6/2007
KR 10-2011-0118379 10/2011
(Continued)

OTHER PUBLICATIONS

International Search Report and Written Opinion dated Mar. 19, 2020 in counterpart International Patent Application No. PCT/KR2019/016153.
(Continued)

*Primary Examiner* — Sunita Reddy
(74) *Attorney, Agent, or Firm* — Nixon & Vanderhye, P.C.

(57) ABSTRACT

An electronic device for providing meditation content corresponding to a stress level of a user, and an operating method thereof are provided. The electronic device includes a communication interface comprising communication circuitry, a memory, and at least one processor operatively coupled to the communication interface and the memory. The memory is configured to store instructions that, when executed, cause the processor to control the electronic device to: receive stress information from at least one collecting device using the communication interface, confirm meditation content corresponding to a stress level based on at least part of the received stress information, confirm at least one executing device related to the confirmed meditation content, and control the execution of the confirmed meditation content and the confirmed at least one executing device using the communication interface.

18 Claims, 15 Drawing Sheets

(52) U.S. Cl.
 CPC ............... *A61M 2021/0022* (2013.01); *A61M 2021/0027* (2013.01); *A61M 2021/0044* (2013.01); *A61M 2021/0066* (2013.01); *A61M 2205/3303* (2013.01); *A61M 2205/3553* (2013.01); *A61M 2205/3561* (2013.01); *A61M 2205/3584* (2013.01); *A61M 2205/50* (2013.01); *A61M 2205/52* (2013.01); *A61M 2230/06* (2013.01)

(58) Field of Classification Search
 CPC .... A61M 2021/005; A61M 2021/0066; A61M 2205/3303; A61M 2205/3553; A61M 2205/3561; A61M 2205/3584; A61M 2205/50; A61M 2205/52; A61M 2230/06; A61M 2205/3313; A61M 2205/332; A61M 2205/3358; A61M 2205/3368; A61M 2205/3592; A61M 2205/609; A61M 2205/80; A61M 2205/8206; A61M 2230/04; A61M 2230/20; A61M 2230/205; A61M 2230/30; A61M 2230/50; A61M 2230/63; G06F 3/165; G06F 3/167; A61B 5/165; H04M 1/72427; H04M 2201/34; H04M 2201/36; H04M 2201/38; G06Q 50/10
 USPC .................................................... 600/26–28
 See application file for complete search history.

(56) References Cited

U.S. PATENT DOCUMENTS

| | | |
|---|---|---|
| 2014/0172910 A1 | 6/2014 | Jung et al. |
| 2015/0297109 A1* | 10/2015 | Garten ................... A61B 5/316 600/28 |
| 2015/0324701 A1* | 11/2015 | Park ....................... G06N 20/00 706/12 |
| 2016/0228640 A1 | 8/2016 | Pindado et al. |
| 2017/0188976 A1 | 7/2017 | Kalra et al. |
| 2017/0273612 A1 | 9/2017 | Kim et al. |
| 2017/0333666 A1 | 11/2017 | Goldberg et al. |
| 2018/0011978 A1 | 1/2018 | Reeckmann |
| 2018/0110960 A1 | 4/2018 | Youngblood et al. |
| 2019/0030278 A1* | 1/2019 | Kremer ................... A61B 5/486 |
| 2020/0368488 A1 | 11/2020 | Sato et al. |

FOREIGN PATENT DOCUMENTS

| | | |
|---|---|---|
| KR | 10-2018-0083188 | 7/2018 |
| KR | 10-2118166 | 5/2020 |

OTHER PUBLICATIONS

Extended European Search Report and Written Opinion dated Nov. 24, 2021 in corresponding European Application No. 19886369.8.

* cited by examiner

ELECTRONIC DEVICE FOR PROVIDING MEDITATION CONTENTS AND OPERATING METHOD THEREOF

CROSS-REFERENCE TO RELATED APPLICATION

This application is based on and claims priority under 35 U.S.C. § 119 to Korean Patent Application No. 10-2018-0146333, filed on Nov. 23, 2018, in the Korean Intellectual Property Office, the disclosure of which is incorporated by reference herein in its entirety.

BACKGROUND

Field

The disclosure relates to an electronic device for providing meditation content corresponding to a stress level of a user, and an operating method thereof.

DESCRIPTION OF RELATED ART

Stress is a factor not only causing various kinds of diseases but also having a great influence on the quality of life. Stress comes without the least respect of time, place, and object, like office workers suffering heavy work, students suffering excessive academic stress, housekeepers complaining about stress and depression resulting from hard housework, aged men feeling stress due to being cut-off from family members and alienation from society, etc. As such, a problem on how this stress is managed is becoming an issue of very significance to modern people always exposed to stress.

In recent years, an electronic device can be used to calculate stress. For example, the electronic device can calculate stress on the basis of a heart rate or heart rate variability.

Commonly, the electronic device can calculate stress on the basis of a heart rate or heart rate variability and express and provide this by a numerical value. This stress information is for enabling a user to previously recognize the existence or non-existence of generation of stress or the possibility of generation thereof, and there is a problem in which it is impossible to directly relieve stress.

The above information is presented as background information only to assist with an understanding of the present disclosure. No determination has been made, and no assertion is made, as to whether any of the above might be applicable as prior art with regard to the present disclosure.

SUMMARY

Embodiments of the present disclosure provide a method and apparatus for recommending meditation contents for reducing a stress of a user in an electronic device.

Embodiments of the present disclosure also provide a method and apparatus for creating an execution environment corresponding to meditation contents in order to improve a stress relief effect in an electronic device.

An electronic device according to various example embodiments of the present disclosure includes a communication interface comprising communication circuitry, a memory, and at least one processor operatively coupled to the communication interface and the memory. The memory stores instructions that, when executed, cause the processor to control the electronic device to: receive stress information from at least one collecting device using the communication interface, confirm meditation content corresponding to a stress level based on at least part of the received stress information, confirm at least one executing device related to the confirmed meditation content, and control the execution of the confirmed meditation content and the confirmed at least one executing device using the communication interface.

A method of operating an electronic device according to various example embodiments of the present disclosure includes receiving stress information from at least one collecting device, confirming meditation content corresponding to a stress level based on at least part of the received stress information, confirming at least one executing device related to the confirmed meditation content, and controlling the execution of the confirmed meditation content and the confirmed at least one executing device.

According to various example embodiments, an electronic device may recommend and provide meditation content corresponding to a stress level of a user, thereby reducing stress of the user. Also, according to various example embodiments, the electronic device may control at least one nearby control device to create an environment suitable to meditation contents reproduction, thereby effectively reducing stress.

An effect which may be obtained from the disclosure is not limited to the effects mentioned above, and other effects not mentioned would be readily understood from the following disclosure by a person having ordinary skill in the art to which the disclosure pertains.

BRIEF DESCRIPTION OF THE DRAWINGS

The above and other aspects, features and advantages of certain embodiments of the present disclosure will be more apparent from the following detailed description, taken in conjunction with the accompanying drawings, in which.

With regard to the description of the drawings, the same or similar reference numerals may be used to refer to the same or similar components.

DETAILED DESCRIPTION

Various example embodiments of the present disclosure are described below in greater detail with reference to the accompanying drawings. In describing example embodiments of the present disclosure, related well-known functions or constructions may not be described in detail where they may obscure the gist of the present disclosure. The terms described below are defined considering functions in the present disclosure, and may be modified in accordance to user and operator intention, practice, etc. Therefore, the definition should be given based on the content throughout the present specification.

Figure 1:
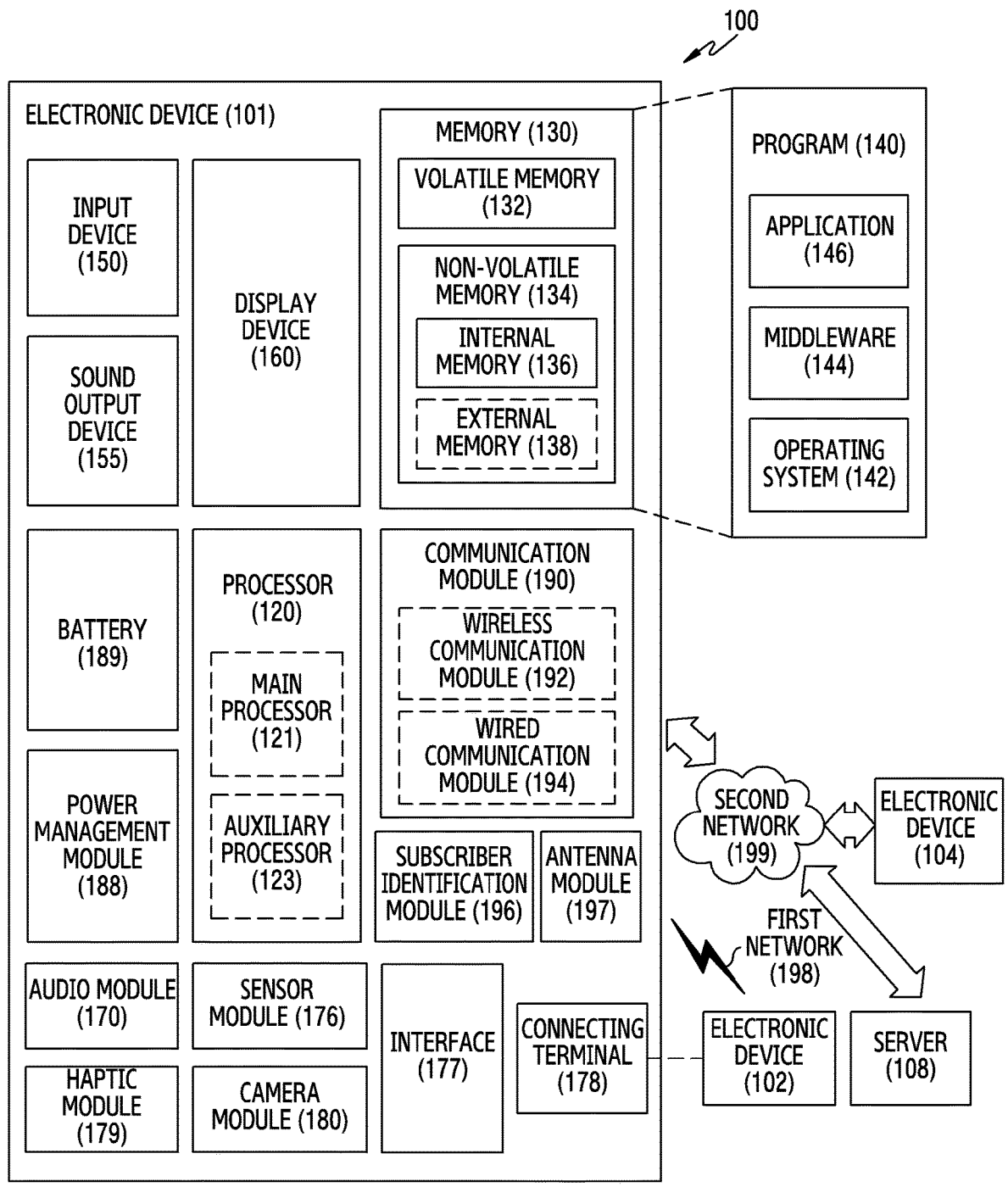
FIG. 1 is a block diagram illustrating an example electronic device within a network environment according to various embodiments.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an example embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an example embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN))). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with", "coupled to," "connected with," or "connected to" another element (e.g., a second element), the element may be coupled with the other element directly (e.g., wiredly), wirelessly, or via a third element.

As used herein, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2:
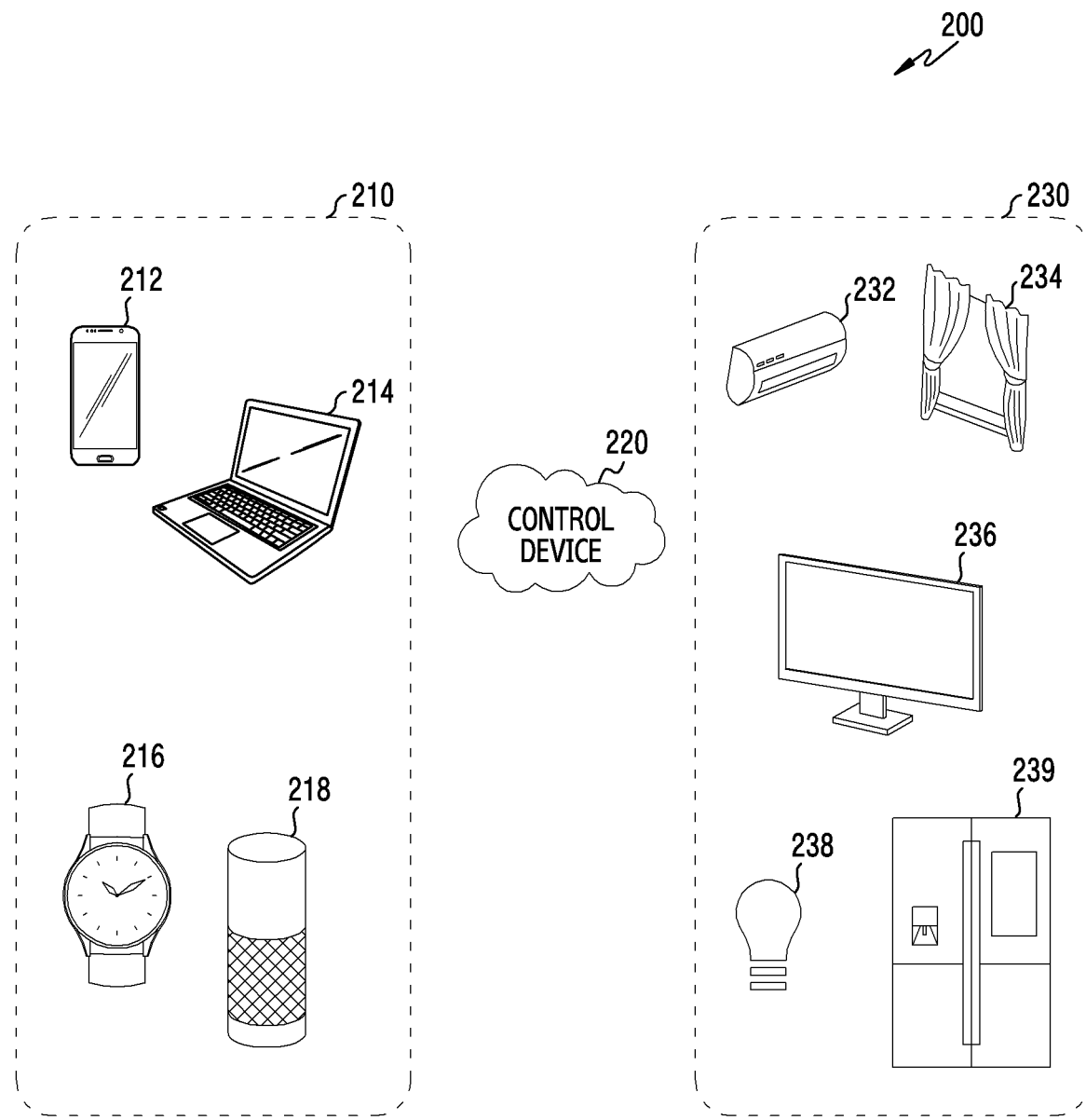
FIG. 2 is a diagram illustrating an example of a meditation contents providing system according to various embodiments.

FIG. 2 is a diagram illustrating an example of a meditation contents providing system 200 according to various embodiments.

Referring to FIG. 2, in various embodiments, the meditation contents providing system 200 may include at least one collecting device 210, a control device 220, and a plurality of executing devices 230.

According to various embodiments, the at least one collecting device 210 may include the electronic device 101 of FIG. 1. Also, the at least one collecting device 210 may include at least one of a mobile electronic device (e.g., a smart phone, a notebook, etc.) 212 or 214 whose carriage is easy, a wearable electronic device (e.g., a watch, a ring, a wristlet, an anklet, shoes, a hat, clothes, glasses, or a necklace-type electronic device) 216 wearable on part of a human body of a user, and/or a wearable electronic device (e.g., an electronic sticker, a smart speaker, a scale, a blood pressure meter, a remote control camera, etc.) 218 able to recognize and communicate with a nearby electronic device. However, this is merely an example, and an embodiment of the present disclosure is not limited to this. As an embodiment, the at least one collecting device 210 may include a human-body mount type electronic device (e.g., a skin pad or tattoo) able to attach to part of the human body of the user and/or a bio implantation type electronic device inserted into the human body. According to an embodiment, the at least one collecting device 210 may be set as one group based on an account of the user.

According to an embodiment, the at least one collecting device 210 may include at least one sensor. Although not illustrated, the at least one sensor may include a first sensor configured to collect information related with health and a second sensor configured to collect information related with at least one of a state of a user or a collection environment.

The first sensor may include a biometric sensor. The biometric sensor may include a heart rate sensor. For example, the biometric sensor may be comprised of a light emitter and a light detector, and may be used to directly or indirectly measure a heart rate of a user and a heart rate variability. According to an embodiment, the first sensor may measure the heart rate variability periodically or at a time point at which a specified event occurs.

The second sensor may include an acceleration sensor, a gyro sensor, and a proximity sensor which may acquire information related with a posture (or motion) and/or movement of the at least one collecting device 210 (or the user). Also, the second sensor may include a temperature/humidity sensor, an ultra-wideband (UWB) sensor, an infrared laser distance measurement (time of flight (ToF)) sensor, and/or an illuminance sensor which may acquire information about a measurement environment (e.g., a collection environment). However, this is merely illustrative, and the present disclosure is not limited to this. For example, the second sensor may include an iris sensor and/or an image sensor which may acquire information for user authentication. For another example, the second sensor may further include a communication module which may recognize a situation or location of the at least one collecting device 210, such as WiFi and GPS. As another example, the second sensor may include at least one of a taste sensor or an olfactory sensor which may acquire information related with at least one of the type of food that a user takes, a taste of the food, or a component of the food. This taste sensor or olfactory sensor may be buried and arranged not only inside the at least one collecting device 210 but also in part (e.g., a tooth, an artificial tooth, etc.) of the human body of the user. In this case, the second sensor buried in part of the human body of the user may deliver the acquired information to the communicatively coupled at least one collecting device 210 as well.

According to an embodiment, the at least one collecting device 210 may obtain a health state (e.g., stress) of a user based on information collected through a sensor (e.g., a biometric sensor). For example, the at least one collecting device 210 may calculate a stress level (e.g., strength) based on heart rate variability data measured through the biometric sensor. For another example, the at least one collecting device 210 may analyze a biometric component (e.g., lactic acid, glucose, etc.) within blood measured through the biometric sensor, to provide the type (e.g., mental stress, physical stress, etc.) of stress.

According to an embodiment, the at least one collecting device 210 may transmit stress information related with a calculated stress to the control device 220. The at least one collecting device 210 may transmit, to the control device 220, the information related with the calculated stress periodically or at a time point at which a specified event occurs. The specified event may be related with entrance or proximity to a registered area. However, this is merely illustrative, and the present disclosure is not limited to this. For example, in response to a specified input (e.g., a voice input, a gesture input, a key input, a touch input, etc.), the information related with stress may be transmitted to the control device 220 as well. Also, the stress information may include at least one of a level (e.g., strength) of stress and/or the type (e.g., mental stress, physical stress, etc.) of stress. In the above description, an example has been explained in which the information related with stress is calculated by the at least one collecting device 210, but this is illustrative, and the present disclosure is not limited to this. For example, the at least one collecting device 210 may transmit collected information (e.g., heart rate data or heart rate variability data) to the control device 220, and the control device 220 may calculate stress based on the received information as well.

According to various embodiments, the control device 220 may be a cloud server which may form communication with the at least one collecting device 210 and the executing devices 230, and some elements of the control device 220 may correspond to the electronic device 101 illustrated in FIG. 1. Also, as mentioned in greater detail below with reference to FIG. 3 below, in response to receiving information related with stress from the at least one collecting device 210, the control device 220 may select at least one meditation content. According to an embodiment, the control device 220 may control the at least one executing device 230 for reproducing meditation content corresponding to a stress level. For example, the control device 220 may control the at least one executing device 230 to reproduce meditation content corresponding to a stress of a first level in a first environment. For instance, the control device 220 may control the lighting device to emit light at a first brightness range, and control an air conditioning system (not shown) to maintain a first temperature range, thereby creating a first environment. For another example, the control device 220 may control the at least one executing device 230 to reproduce meditation content corresponding to a stress of a second level in a second environment. For instance, the control device 220 may control the lighting device 238 to emit light at a second brightness range different from the first brightness range, and control the air conditioning system (not shown) to maintain a second temperature range different from the first temperature range, thereby creating a second environment. In the above description, the lighting device 238 and the air conditioning system (not shown) have been explained as the executing device 230 controlled to create an environment of reproduction of meditation contents, but this is illustrative, and the present disclosure is not limited to this. For example, the control device 220 may control the various executing devices 230, thereby creating an environment of reproduction of meditation contents.

According to various embodiments, the plurality of executing devices 230 may include, for example, and without limitation, an air conditioner 232, a motor curtain 234, a television 236, a lighting device 238, a refrigerator 239, etc. Although not illustrated, the plurality of executing devices 230 of various embodiments may further include a temperature control device, a crime prevention device, a gas valve control device, a door locking device, a dehumidifying device, an audio device, a video device, and/or an aromatic diffuser. According to an embodiment, the plurality of executing devices 230 may be set as one group based on an account of a user, and some elements of the executing device 230 may correspond to the electronic device 101 illustrated in FIG. 1.

According to an embodiment, the plurality of executing devices 230 may each include a communication circuit, thereby forming communication with the control device 220 by a specified protocol (e.g., Bluetooth, WiFi, Zigbee, etc.), to transceive various information. For example, the plurality of executing devices 230 may transmit information (e.g., device on/off information) about its own operation state to the control device 220. Also, the plurality of executing devices 230 may receive a control message (e.g., an on/off control command of a device, other operation control commands of the device, etc.) from the control device 220, to execute an operation corresponding to the control message. According to an embodiment, the executing device 230 may transmit the execution result of the operation corresponding to the control message, to the control device 220.

In the above-described embodiment, the collecting device 210, the control device 220 and the executing device 230 have been explained as mutually separated constructions, but this is illustrative and the present disclosure is not limited to this. For example, at lease one of the collecting device 210, the control device 220 and the executing device 230 may execute a function of another device. For instance, the control device 220 may additionally execute a function of the collecting device 210, and the executing device 230 may additionally execute the function of the collecting device 210 as well.

Figure 3:
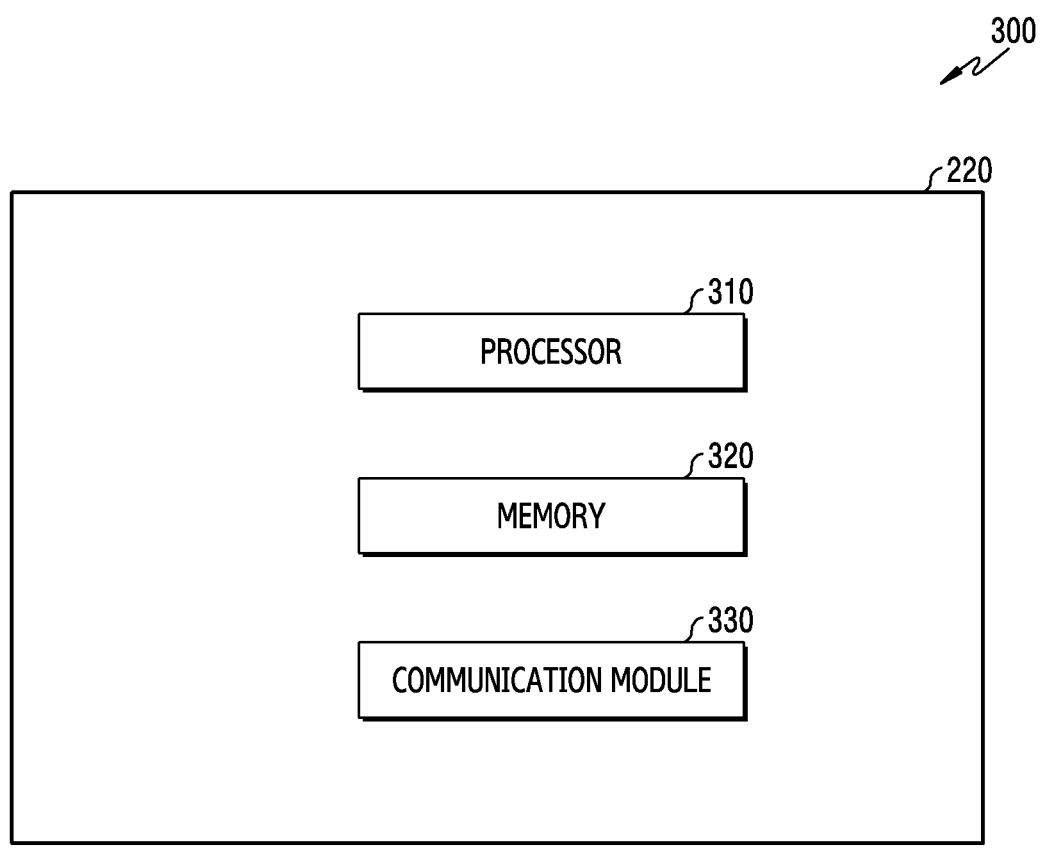
FIG. 3 is a block diagram illustrating an example configuration of a control device according to various embodiments.
Figures 4A, 4B, 4C:
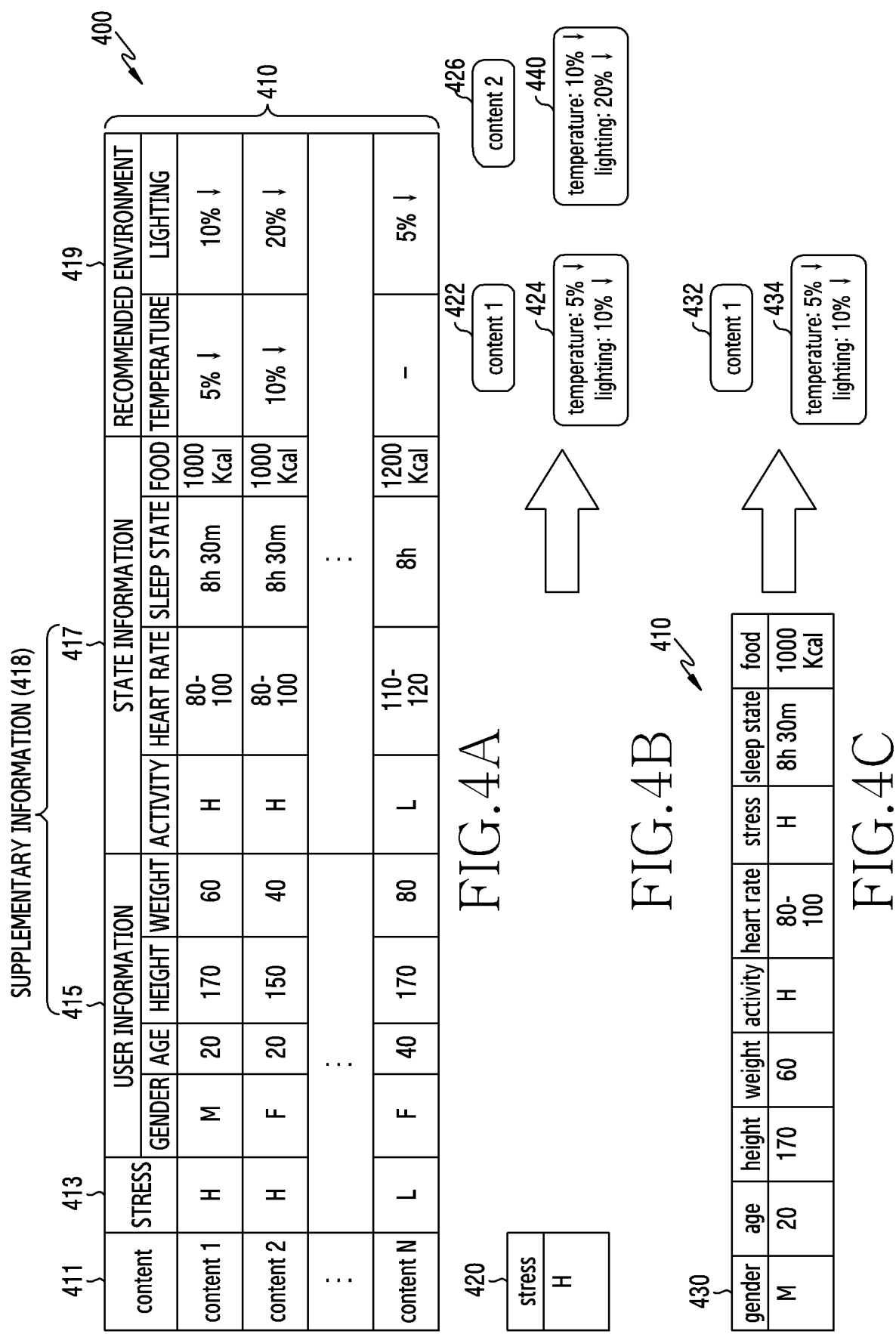
FIGS. 4A, 4B and 4C are diagrams illustrating an example operation of selecting meditation content in a control device according to various embodiments.

FIG. 3 is a block diagram 300 illustrating an example configuration of the control device 220 according to various embodiments. FIGS. 4A, 4B and 4C are diagrams illustrating an example operation 400 of selecting meditation content in the control device 220 according to various embodiments.

Referring to FIG. 3, some elements of the control device (e.g., the control device 220 of FIG. 2) may correspond to the electronic device 101 illustrated in FIG. 1. For example, the control device 220 may include a processor (e.g., including processing circuitry) 310, a memory 320 and a communication module (e.g., including communication circuitry) 330, and may operate as a cloud server as mentioned earlier as well.

According to various embodiments, the processor 310 may include various processing circuitry and select at least one meditation content corresponding to stress based on information received from a collecting device (e.g., at least one collecting device 210 of FIG. 2). The processor 310 may compare stress information received from the collecting device 210 and meta information stored in the memory 320, to select meditation content corresponding to a stress level. For example, as illustrated in FIG. 4A, meta information 410 may be information matching a stress level 413 to each of a plurality of meditation contents (e.g., the N number of meditation contents) 411. Also, the meta information 410 may further include supplementary information 418 which includes at least one of user information (e.g., a gender, an age, a height, a weight, etc.) 415, user state information (e.g., an activity state, a sleeping state, and an eating habit state) 417, and/or environment information (e.g., a temperature, a humidity, a season, etc.) (not shown) as well. Also, the meta information 410 may include information about a recommended environment 419 for each of the meditation contents 411 as well. The information about the recommended environment 419 may be related with an operation mode of a peripheral executing device (e.g., the executing device 230 of FIG. 2) suitable to stress relief.

According to an embodiment, the processor 310 may select at least one meditation content corresponding to a stress level, based on stress information provided from the collecting device 210. Also, the processor 310 may confirm at least one executing device 230 intended to be controlled to create an execution environment (or a recommended environment) for the selected meditation content. For example, in response to receiving stress information 420 representing a stress strength (e.g., high (H)) of a first level from the collecting device 210, as illustrated in FIG. 4B, the processor 310 may select a first mediation content (e.g., content 1) 422 and a second meditation content (e.g., content 2) 426 which are matched with the stress strength of the first level among the meditation contents 411 included in the stored meta information 410. Also, through the meta information 410, the processor 310 may confirm that there is a need to control a temperature (e.g., an indoor temperature) and a brightness (e.g., an indoor brightness) of an execution space in order to create a recommended environment for the selected first meditation content 422 and second meditation content 426. At this time, through the meta information 410, the processor 310 may identify an operation mode of the executing device 230 as well. For instance, as illustrated, at the time of execution of the first meditation content 422, the processor 310 may identify an operation mode of an air conditioner (e.g., the air conditioner 232 of FIG. 2) for decreasing a current temperature within a first temperature range (e.g., 5%) and an operation mode 424 of a lighting device (e.g., the lighting device 238 of FIG. 2) for decreasing a current brightness within a first brightness range (e.g., 10%). Also, as illustrated, at the time of execution of the second meditation content 426, the processor 310 may identify an operation mode of the air conditioner 232 for decreasing a current temperature within a second temperature range (e.g., 10%) and an operation mode 440 of the lighting device 238 for decreasing a current brightness within a second brightness range (e.g., 20%). For another example, although not illustrated, in response to receiving stress information representing a stress strength (e.g., low (L)) of a second level from the collecting device 210, the processor 310 may select meditation content (e.g., content N) matched with the stress strength of the second level among the stored meta information 410.

According to another embodiment, the processor 310 may additionally receive at least one of the user information 415 and the state information 417 from the collecting device 210, and use this for selection of the meditation contents 411. For example, as illustrated in FIG. 4C, in response to receiving information 430 capable of specifying (417) stress information representing a stress strength (e.g., high (H)) of a first level, the user information 415 capable of specifying a user, and the user state from the collecting device 210, the processor 310 may select a first meditation content (e.g., content 1) 432 matched with a stress level, the user information and the supplementary information among the meditation contents 411 included in the stored meta information 410. Also, through the meta information 410, the processor 310 may confirm that there is a need to control a temperature (e.g., an indoor temperature) and a brightness (e.g., an indoor brightness) of an execution space in order to create a recommended environment for the selected first meditation content 432. At this time, through the meta information 410, the processor 310 may identify an operation mode 434 of the executing device 230 as well.

According to an embodiment, in response to confirming the at least one executing device 230, the processor 310 may process to execute the selected meditation contents 411.

According to various embodiments, the communication module 330 may include various communication circuitry and establish a communication channel between the control device 220 and the collecting device 210 and/or the control device 220 and the executing device 230. The communication module 330 may include at least one wireless (e.g., mobile communication, WiFi, and/or Bluetooth, etc.) communication circuitry and/or at least one wired (e.g., high definition multimedia interface (HDMI), display port (DP), or universal serial bus (USB), etc.) communication circuitry. For example, the control device 220 may receive information collected by the collecting device 210 through the communication module 330. Also, the control device 220 may transmit a meditation contents 411 execution command and an executing device 230 control command through the communication module 330.

Figure 5A:
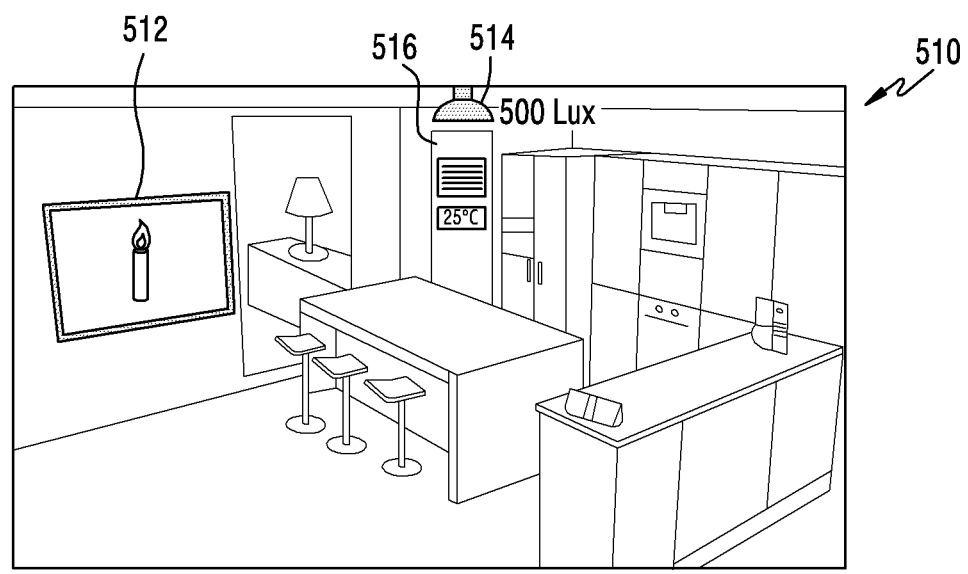
FIGS. 5A and 5B are diagrams illustrating an example situation of providing meditation contents in an electronic device according to various embodiments.
Figure 5B:
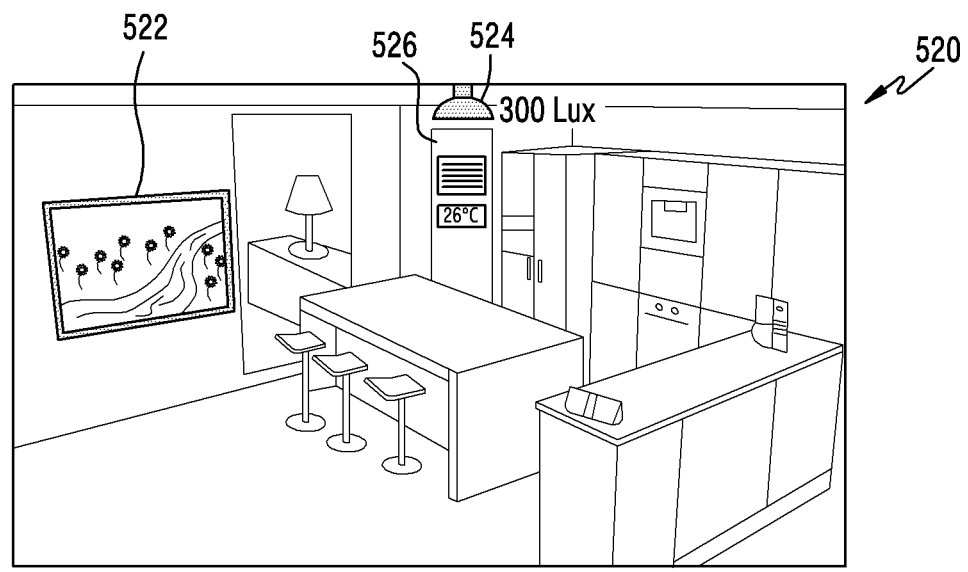

FIG. 5A and FIG. 5B are diagrams illustrating example situations 510 and 520 of providing meditation contents in an electronic device according to various embodiments. The electronic device of FIGS. 5A and 5B may be the control device 220 of FIG. 3.

Referring to FIG. 5A to FIG. 5B, the electronic device may provide suitable meditation contents (e.g., the meditation contents 411 of FIG. 4) to a user based on the type of stress received from the collecting device 210 and previously stored meta information.

The type of stress may be divided into mental stress and physical stress. The mental stress may refer, for example, to a mental fatigue such as tension, anxiety, concern provided by an external stimuli, and the physical stress may refer, for example, to a physical fatigue such as the loss of appetite, the occurrence of emesis, and the occurrence of a heart disease provided by an external stimuli. The aforementioned type of stress is illustrative, and an embodiment of the present disclosure is not limited to this. In an embodiment, the stress may be divided into strong stress and weak stress based on a stress index as well.

According to an embodiment, in response to a user's stress being identified as mental stress, as illustrated in FIG. 5A, the electronic device may provide meditation contents for guiding breathing meditation in order to reduce the mental stress. For example, the electronic device may control a video device to reproduce contents (e.g., a candlelight screen) 512 guiding the breathing meditation and control an audio device to reproduce music (not shown) helpful for mental stability. Also, the electronic device may set an indoor brightness (e.g., 500 lux) 514 and an indoor temperature (e.g., 25° C.) 516 corresponding to an environment helpful for the breathing meditation.

According to another embodiment, in response to a user's stress being identified as physical stress, as illustrated in FIG. 5B, the electronic device may control the video device to reproduce meditation contents (e.g., a mountain stream sound) 522 guiding sleeping meditation in order to reduce the physical stress and control the audio device to reproduce music (not shown) helpful for good sleep. Also, the electronic device may set an indoor brightness (e.g., 300 lux) 524 and an indoor temperature (e.g., 25° C.) 526 corresponding to an environment helpful for the sleeping meditation.

According to various example embodiments, an electronic device (e.g., the control device 220) may include a communication interface comprising communication circuitry (e.g., the communication module 330), a memory (e.g., the memory 320), and at least one processor (e.g., the processor 310) operatively coupled to the communication interface and the memory. According to an embodiment, the memory may store instructions that, when executed, cause the processor to control the electronic device to: receive stress information from at least one collecting device (e.g., the collecting device 210) using the communication interface, confirm meditation content corresponding to a stress level based on at least part of the received stress information, confirm at least one executing device (e.g., the executing device 230) related to the confirmed meditation content, and control the execution of the confirmed meditation content and the confirmed at least one executing device using the communication interface.

According to an example embodiment, the memory may be configured to store meta information (e.g., the meta information 410) matching a stress level to each of a plurality of meditation contents. Also, the instructions may, when executed, cause the processor to control the electronic device to confirm the meditation content corresponding to the stress level based on at least part of a comparison result of the received stress information and the stored meta information.

According to an example embodiment, the instructions, when executed, may cause the processor to control the electronic device to: in response to receiving stress information representing a stress of a first level using the communication interface, identify first meditation content as the confirmed meditation content, and in response to receiving stress information representing a stress of a second level using the communication interface, identify second meditation content as the confirmed meditation content.

According to an example embodiment, the meta information may further include at least one of user information, a user state, or environment information. Also, the instructions may, when executed, cause the processor to control the electronic apparatus to: in response to receiving supplementary information from the collecting device using the communication interface, confirm the meditation content corresponding to the stress level based on at least part of a comparison result of the received supplementary information and the stored meta information.

According to an example embodiment, the memory may be configured to store meta information in which a recommended environment is matched to each of a plurality of meditation contents. Also, the instructions may, when executed, cause the processor to control an operation of the at least one executing device based on at least part of the meta information.

According to an example embodiment, the instructions may, when executed, cause the processor to, in response to the first meditation content being confirmed, control the at least one executing device to execute the first meditation content in a first environment, and in response to the second meditation content being confirmed, control the at least one executing device to execute the second meditation content in a second environment different from the first environment.

According to an embodiment, the stress information may further include the type of stress. Also, the instructions may, when executed, cause the processor to control the electronic device to: confirm the meditation content corresponding to the type of stress.

According to an example embodiment, the instructions may, when executed, cause the processor to control the electronic device to: confirm at least one executing device related with the confirmed meditation content among a plurality of executing devices set as a group based on an account of a user.

According to an example embodiment, the instructions may, when executed, cause the processor to control the collecting device to guide the viewing of the meditation content.

According to an example embodiment, the instructions may, when executed, cause the processor to control the electronic device to: in response to receiving stress information from the collecting device using the communication interface, identify that the collecting device enters a previously registered area.

Figure 6:
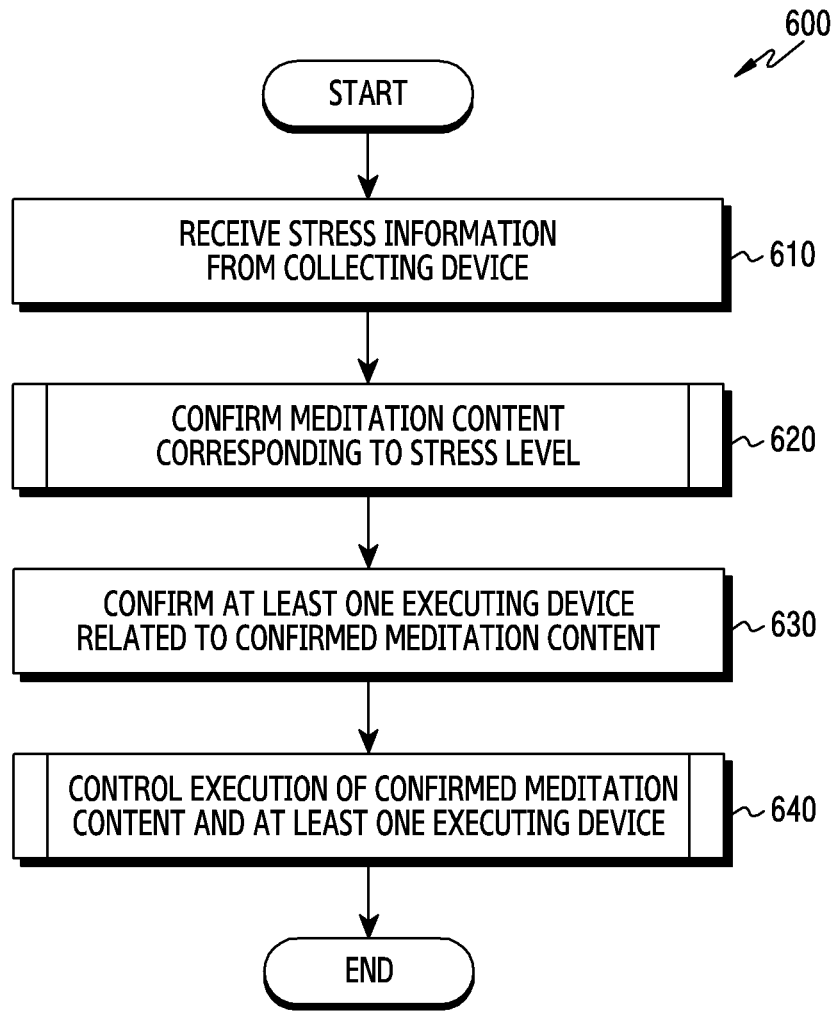
FIG. 6 is a flowchart illustrating an example operation of providing meditation contents in an electronic device according to various embodiments.

FIG. 6 is a flowchart 600 illustrating an example operation of providing meditation contents in an electronic device according to various embodiments. In an example embodiment below, respective operations may be performed in sequence as well, but are not necessarily performed in sequence. For example, the order of respective operations may be changed as well, and at least two operations may be performed in parallel as well. The electronic device of FIG. 6 may be the control device 220 of FIG. 3.

Referring to FIG. 6, in operation 610, the electronic device (e.g., the processor 310 of FIG. 3) of various embodiments may receive stress information from the at least one collecting device 210. The stress information may include at least one of a level (e.g., strength) of stress and/or the type (e.g., mental stress, physical stress, etc.) of stress.

In operation 620, the electronic device (e.g., the processor 310 of FIG. 3) of various embodiments may confirm meditation content corresponding to a stress level. The processor 310 may compare the stress information with meta information stored in the memory 320, to select the meditation content corresponding to the stress level. For example, as mentioned earlier through FIG. 4A, the meta information may be information matching the stress level 413 to each of the meditation contents 411. According to an embodiment, the processor 310 may confirm at least one meditation content matched with the stress information received from the collecting device 210 among the meditation contents 411 included in the meta information 410. For example, as illustrated in FIG. 4B, the processor 310 may select meditation content suitable to user's stress relief.

In operation 630, the electronic device (e.g., the processor 310 of FIG. 3) of various embodiments may confirm at least one executing device 230 related to the confirmed meditation content. The executing device 230 may include an executing device of a first group for executing the confirmed meditation content and an executing device of a second group for creating an environment which is helpful for stress relief at the time of execution of the meditation content. For example, the executing device of the first group may include at least one of a video device (e.g., a television, a monitor, etc.) and an audio device (e.g., a speaker), and the executing device of the second group may include at least one of an air conditioner, a motor curtain, a lighting device or an aromatic diffuser. According to an embodiment, the electronic device may confirm at least one executing device of a first group and/or at least one executing device of a second group based on recommended environment information matched with the selected meditation contents.

In operation 640, the electronic device (e.g., the processor 310 of FIG. 3) of various embodiments may control the execution of the confirmed meditation content and the at least one executing device 230. According to an embodiment, the processor 310 may control the executing device 230 based on a recommended environment matched with the selected meditation content. For example, the processor 310 may set an operation mode of the at least one executing device 230 to create the recommended environment.

Figure 7:
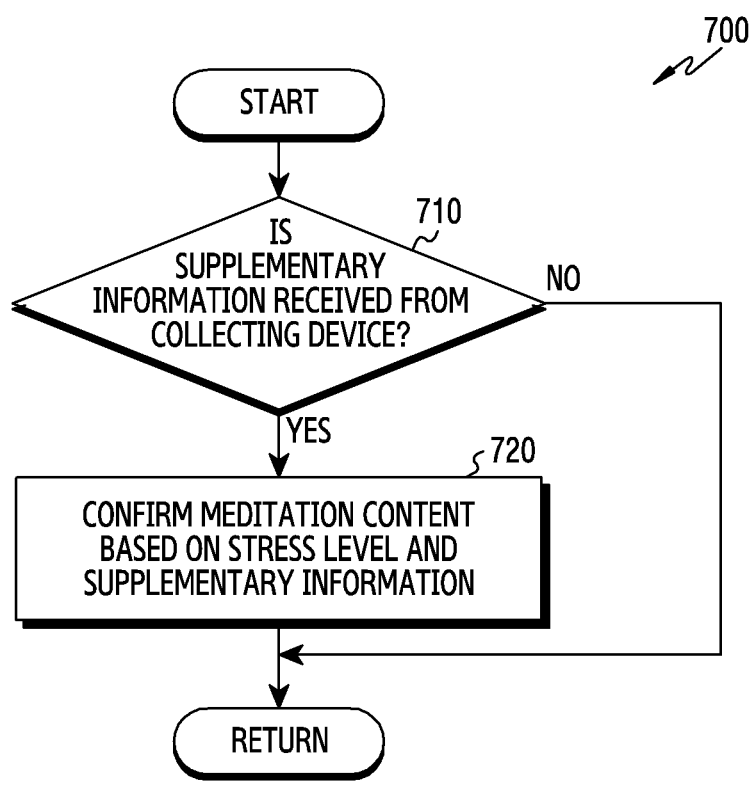
FIG. 7 is a flowchart illustrating an example operation of selecting meditation content in an electronic device according to various embodiments.

FIG. 7 is a flowchart 700 illustrating an example operation of selecting meditation content in an electronic device according to various embodiments. Operations of FIG. 7 explained below may be ones representing various embodiments of operation 620 of FIG. 6. Also, in an embodiment below, respective operations may be performed in sequence as well, but are not necessarily performed in sequence. For example, the order of respective operations may be changed as well, and at least two operations may be performed in parallel as well. The electronic device of FIG. 7 may be the control device 220 of FIG. 3.

Referring to FIG. 7, in operation 710, the electronic device (e.g., the processor 310 of FIG. 3) of various embodiments may identify whether supplementary information (e.g., the supplementary information 418 of FIG. 4) is received from the collecting device 210. The supplementary information may include at least one of user profile information (e.g., a gender, an age, a height, a weight, etc.) (e.g., the user information 415 of FIG. 4), user state (e.g., an activity state, a sleeping state, and an eating habit state) information (e.g., the state information 417 of FIG. 4), and environment information (e.g., a temperature, a humidity, a season, etc.) at stress measurement.

In response to confirming that the supplementary information is not received ("No" in operation 710), the electronic device (e.g., the processor 310 of FIG. 3) of various embodiments may select meditation content based on a stress level. For example, as mentioned earlier through operation 620 of FIG. 6, the processor 310 may confirm the meditation content corresponding to the stress level.

In response to confirming that the supplementary information is received ("Yes" in operation 710), in operation 720, the electronic device (e.g., the processor 310 of FIG. 3) of various embodiments may confirm meditation content based on the stress level and the supplementary information. According to an embodiment, as mentioned earlier through FIG. 4A, the meta information 410 may further include the supplementary information 417 which includes at least one of the user information (e.g., a gender, an age, a height, a weight, etc.) 415, a user state (e.g., an activity state, a sleeping state, and an eating habit state) or environment information (e.g., a temperature, a humidity, a season, etc.) as well. The processor 310 may compare stress information and the received supplementary information with the meta information 410 stored in the memory 320, to select the meditation content corresponding to the stress level. For example, as illustrated in FIG. 4C, the processor 310 may select meditation contents suitable to user stress relief.

Figure 8A:
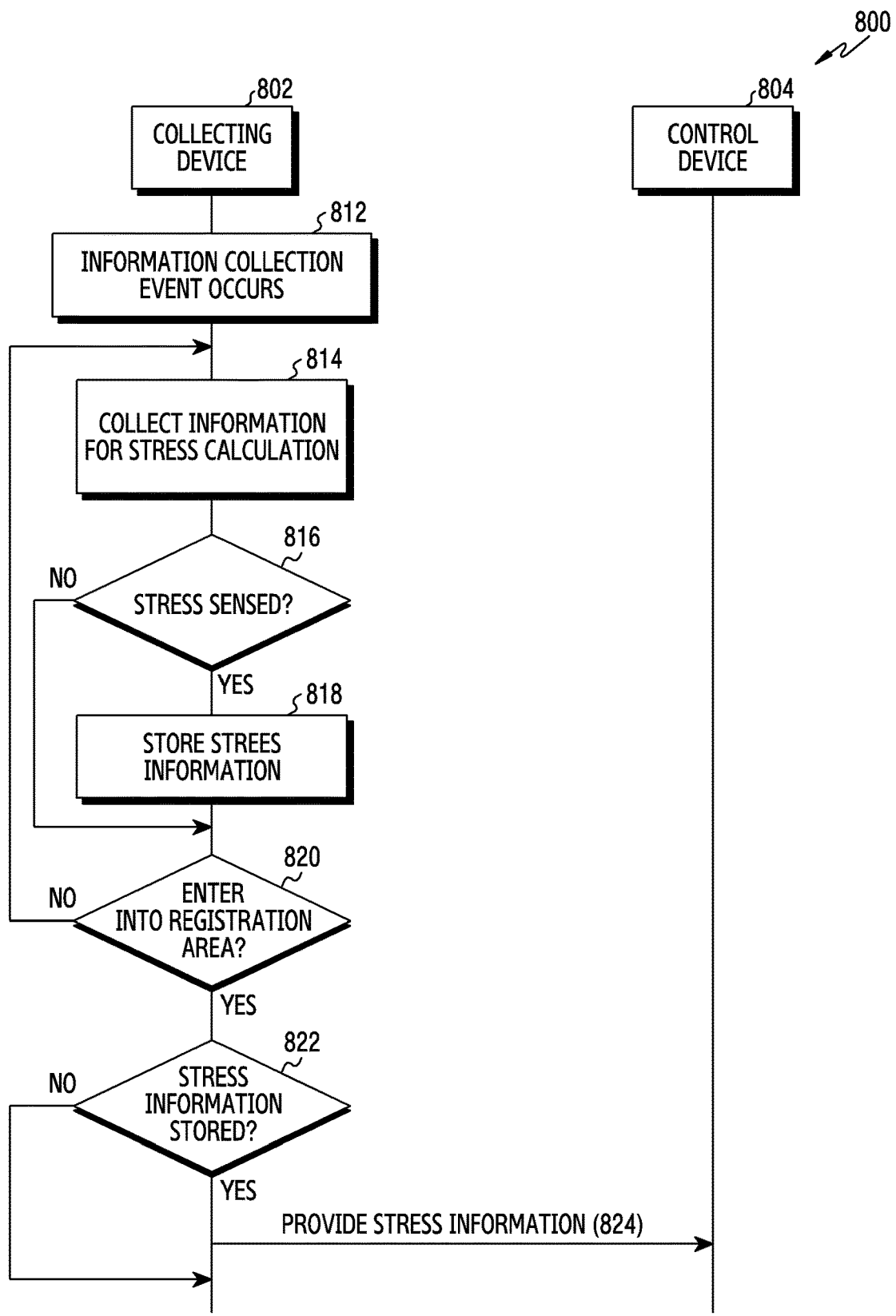
FIG. 8A is a flowchart illustrating an example operation of measuring stress in a system according to various embodiments.

FIG. 8A is a flowchart 800 illustrating an example operation of measuring stress in a system according to various embodiments.

As illustrated in FIG. 8A, according to various embodiments, stress may be measured by operations of a collecting device 802 (e.g., the collecting device 210 of FIG. 2) and a control device 804 (e.g., the control device 220 of FIG. 2).

Referring to FIG. 8A, in operation 812, the collecting device 802 may sense the occurrence of an information collection event. According to an embodiment, as mentioned earlier, the collecting device 802 may be an electronic device in which body wearing is possible or body mount is possible. In this case, in response to sensing the electronic device being worn or mounted on a body, the collecting device 802 may identify that the information collection event has occurred. However, this is merely an example, and an embodiment of the present disclosure is not limited to this and various embodiments may be applied. For instance, in response to sensing a previously specified input (e.g., a voice input, a gesture input, a key input, a touch input, etc.), the collecting device 802 may identify that the information collection event has occurred as well.

In response to sensing the occurrence of the information collection event, in operation 814, the collecting device 802 may collect information for stress calculation. The information for stress calculation may include a heart rate and/or heart rate variability. For example, the collecting device 802 may continuously or periodically collect the information for stress calculation.

In operation 816, the collecting device 802 may identify whether stress on a user is sensed based on the collected information. For example, the collecting device 802 may calculate a stress level (e.g., a strength, an index, etc.) based on a user's heart rate or heart rate variability. Also, in response to a stress level of a specified level or more being calculated, the collecting device 802 may identify that stress has been sensed.

In response to it being identified that the stress has been sensed ("Yes" in operation 816), in operation 818, the collecting device 802 may store stress information in the collecting device (e.g., the memory 320 of FIG. 3).

After storing the stress information or in response to identifying that the stress has not been sensed ("No" in operation 816), in operation 820, the collecting device 802 may identify entrance or non-entrance into a registration area. According to an embodiment, the collecting device 802 may identify entrance into the registration area using at least one of GPS, WiFi, Bluetooth, BLE, sensor, and near field communication (NFC). For instance, the registration area may include a geo-fence.

In response to the entrance into the registration area not being identified ("No" in operation 820), the collecting device 802 may collect information for stress calculation. According to an embodiment, until the entrance into the registration area is identified, the collecting device 802 may collect the information for stress calculation. For example, the collecting device 802 may continuously or periodically monitor whether a situation in which a user feels stress occurs or a situation in which stress is relieved during movement occurs. For instance, in response to the situation in which stress is relieved during movement occurring, the collecting device 802 may delete the stored stress information or store information representing the situation in which stress is relieved as well.

In response to the entrance into the registration area being identified ("Yes" in operation 820), in operation 822, the collecting device 802 may identify the storage or non-storage of the stress information.

In response to it being identified that the stress information has been stored ("Yes" in operation 822), in operation 824, the collecting device 802 may provide the stress information to the control device 804. For example, the stress information may include the calculated stress level (e.g., strength, index, etc.).

Accordingly, in response to receiving the stress information, the control device 804 may control the execution of meditation contents. For example, the control device 804 may perform an operation related with at least one of operation 630 and operation 640 of FIG. 6.

Also, in response to it being identified that the stress information has not been stored ("No" in operation 822), the collecting device 802 may identify that it is a situation in which the user does not feel stress and thus, may not provide separate information to the control device 804.

In the above description, an example has been explained in which stress information is calculated by the collecting device 802, but this is illustrative, and the present disclosure is not limited to this. For example, the collecting device 802 may provide non-processed biometric information (raw data) to the control device 804, and accordingly to this, the control device 804 may calculate stress based on the received biometric information as well. In this case, the control device 804 may calculate stress based on the received biometric information as well. Additionally, the control device 804 may obtain various information such as a blood pressure, a blood sugar, arrhythmia, an oxygen saturation, etc. based on the received biometric information.

Figure 8B:
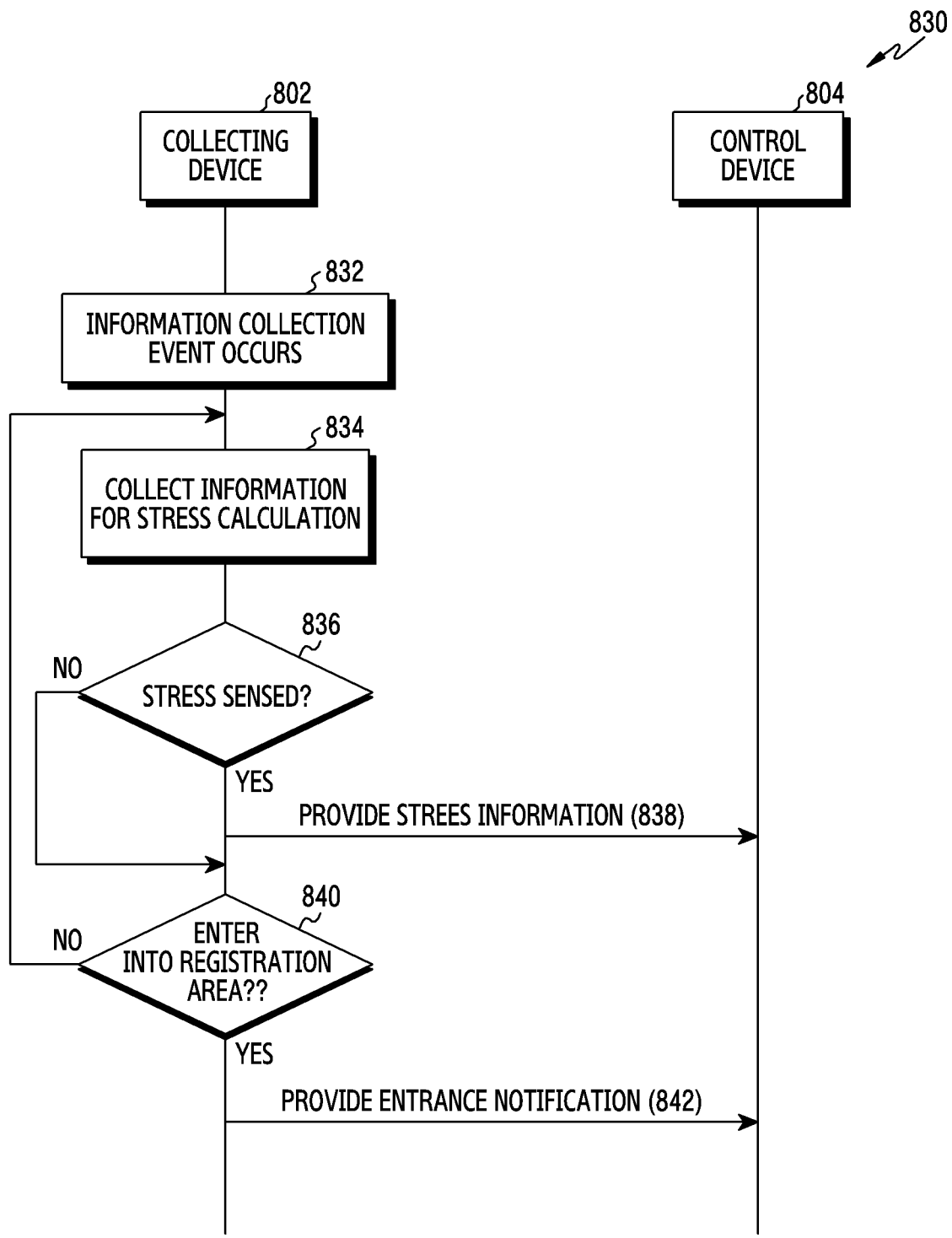
FIG. 8B is a flowchart illustrating another example operation of measuring stress in a system according to various embodiments.

FIG. 8B is a flowchart 830 illustrating an example operation of measuring stress in a system according to various embodiments.

As illustrated in FIG. 8B, according to various embodiments, stress may be measured by operations of a collecting device 802 (e.g., the collecting device 210 of FIG. 2) and a control device 804 (e.g., the control device 220 of FIG. 2).

Referring to FIG. 8B, in operation 832, the collecting device 802 may sense the occurrence of an information collection event. According to an embodiment, as mentioned earlier, as an example embodiment, the collecting device 802 may be an electronic device in which body wearing is possible or body mount is possible. In this case, in response to sensing the body wearing or the body mount, the collecting device 802 may identify that the information collection event has occurred.

In response to sensing the occurrence of the information collection event, in operation 834, the collecting device 802 may collect information for stress calculation. The information necessary for stress calculation may include a heart rate and/or heart rate variability. For example, the collecting device 802 may continuously or periodically collect the information necessary for stress calculation.

In operation 836, the collecting device 802 may identify whether stress on a user is sensed based on the collected information. For example, the collecting device 802 may calculate a stress level (e.g., a strength, an index, etc.) based on a user's heart rate or heart rate variability. Also, in response to a stress level of a specified level or more being calculated, the collecting device 802 may identify that stress has been sensed.

In response to it being identified that the stress has been sensed ("Yes" in operation 836), in operation 838, the collecting device 802 may provide stress information to the control device 804. For example, the stress information may include the calculated stress level (e.g., strength, index, etc.).

After providing the stress information to the control device 804 or in response to identifying that the stress has not been sensed ("No" in operation 836), in operation 840, the collecting device 802 may identify entrance or non-entrance into a registration area. According to an embodiment, the collecting device 802 may identify entrance into the registration area using at least one of GPS, WiFi, Bluetooth, BLE, sensor, and near field communication (NFC).

In response to the entrance into the registration area not being identified ("No" in operation 840), the collecting device 802 may collect information for stress calculation while identifying the entrance or non-entrance into the registration area.

In response to the entrance into the registration area being identified ("Yes" in operation 840), in operation 842, the collecting device 802 may provide a notification of entrance into the registration area to the control device 804. Accordingly, in response to receiving the entrance notification, the control device 804 may control the execution of meditation contents. For example, the control device 804 may perform an operation related with at least one of operation 630 and operation 640 of FIG. 6.

The aforementioned operation of FIG. 8B has a difference with the aforementioned operation of FIG. 8A in an aspect in which the collecting device 802 provides the stress information to the control device 804 before the entrance into the registration area, in other words, in response to the stress sensing. For example, according to an embodiment of FIG. 8B, before the collecting device 802 enters the registered area, the control device 804 may previously identify meditation contents suitable to stress relief and an environment of execution of the meditation contents based on the stress information, and may create the environment of execution of the meditation contents at the same time when the collecting device 802 enters the registered area.

Also, in the above description, an example has been explained in which the stress information is calculated by the collecting device 802, but this is illustrative, and the present disclosure is not limited to this. For example, as described above, the collecting device 802 may provide non-processed biometric information (raw data) to the control device 804, and accordingly to this, the control device 804 may calculate stress based on the received biometric information as well.

Figure 9:
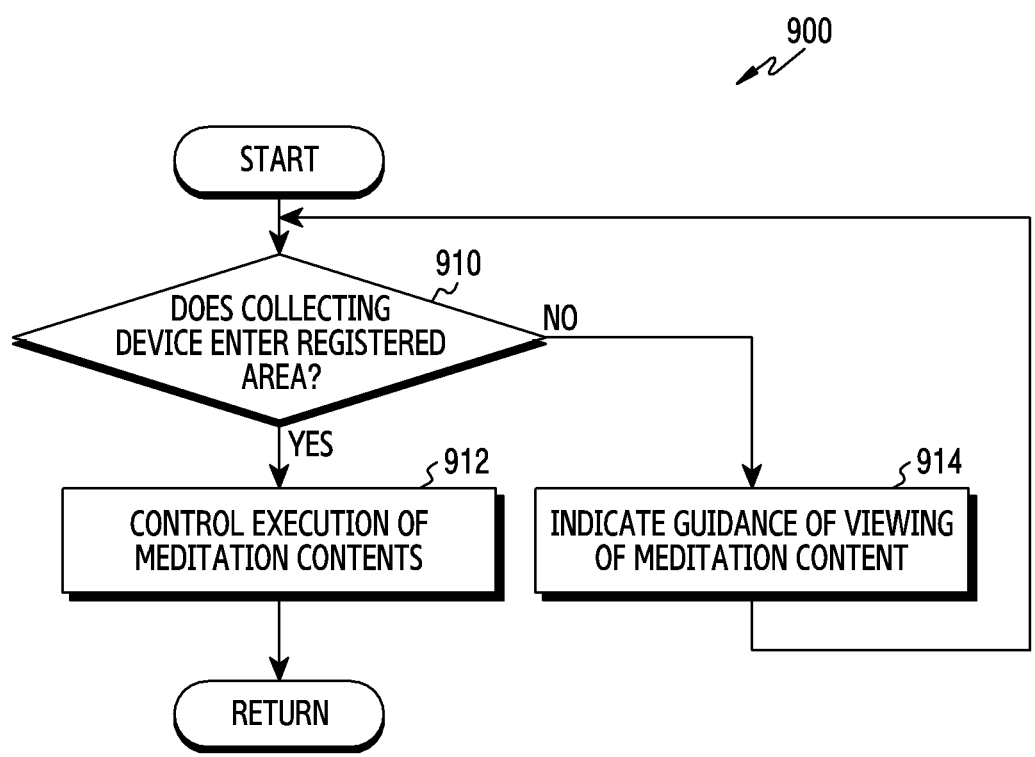
FIG. 9 is a flowchart illustrating an example operation of providing meditation contents in an electronic device according to various embodiments.
Figure 10:
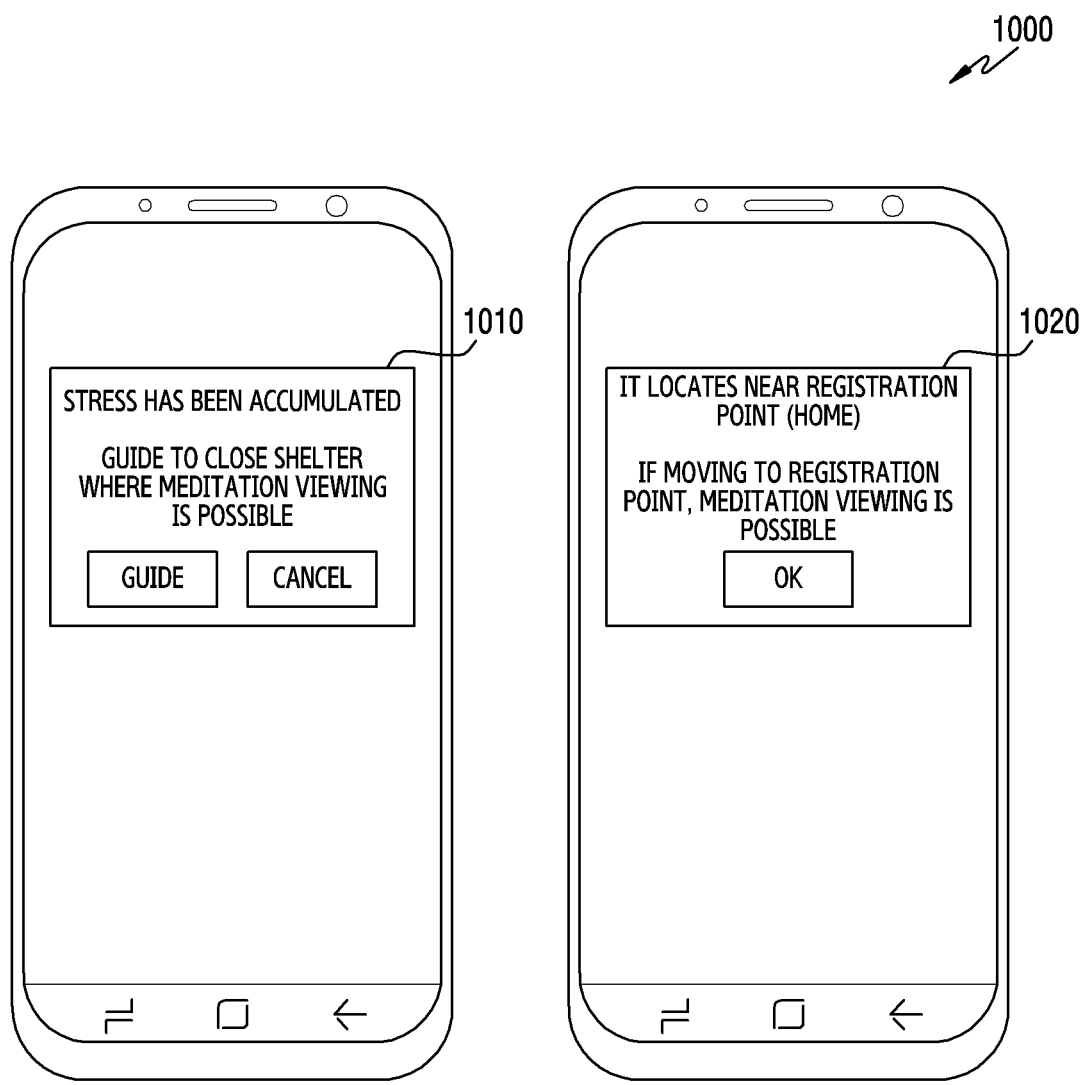
FIGS. 10A and 10B are diagrams illustrating an example situation of guiding the viewing of meditation contents in a collecting device according to various embodiments.

FIG. 9 is a flowchart 900 illustrating an example operation of providing meditation contents in an electronic device according to various embodiments. FIGS. 10A and 10B are diagrams 1000 illustrating an example situation of guiding the viewing of meditation contents in a collecting device. Operations of FIG. 9 explained below may be ones representing various embodiments of operation 640 of FIG. 6. Also, in an embodiment below, respective operations may be performed in sequence as well, but are not necessarily performed in sequence. For example, the order of respective operations may be changed as well, and at least two operations may be performed in parallel as well. The electronic device of FIG. 9 may be the control device 220 of FIG. 3.

Referring to FIG. 9, in operation 910, the electronic device (e.g., the processor 310 of FIG. 3) of various embodiments may identify whether the collecting device 210 enters a registered area. According to an embodiment, in response to receiving an entrance notification from the collecting device 210, the processor 310 may identify that the collecting device 210 enters the registered area.

In response to identifying that the collecting device 210 enters the registered area of various embodiments ("Yes" in operation 910), in operation 912, the electronic device (e.g., the processor 310 of FIG. 3) may control the execution of meditation contents. According to an embodiment, the processor 310 may control at least one executing device (e.g., a television, a monitor, a speaker, etc.) of a first group to execute meditation content. Also, the processor 310 may control at least one executing device (e.g., an air conditioner, a motor curtain, a dehumidifier, a lighting device, an aromatic diffuser, etc.) of a second group in order to create an environment which is helpful for stress relief at the time of meditation content execution.

In response to identifying that the collecting device 210 does not enter the registered area of various embodiments ("No" in operation 910), in operation 914, the electronic device (e.g., the processor 310 of FIG. 3) may indicate the guidance of viewing of meditation contents. According to an embodiment, the processor 310 may indicate the viewing guidance by providing the collecting device 210 with notification information notifying that a preparation of execution of meditation contents is completed. The collecting device 210 receiving this notification information may provide guide information guiding the viewing of meditation contents. For example, as illustrated in FIG. 10A, when a user who wears the collecting device 210 is in a driving state, the collecting device 210 may provide guide information 1010 guiding to a place where meditation viewing is possible. For another example, as illustrated in FIG. 10B, when the user who wears the collecting device 210 is in a state of being within a specified proximity to the registered area (e.g., a registration point), the collecting device 210 may provide guide information 1020 guiding to the registration point as well.

Figure 11:
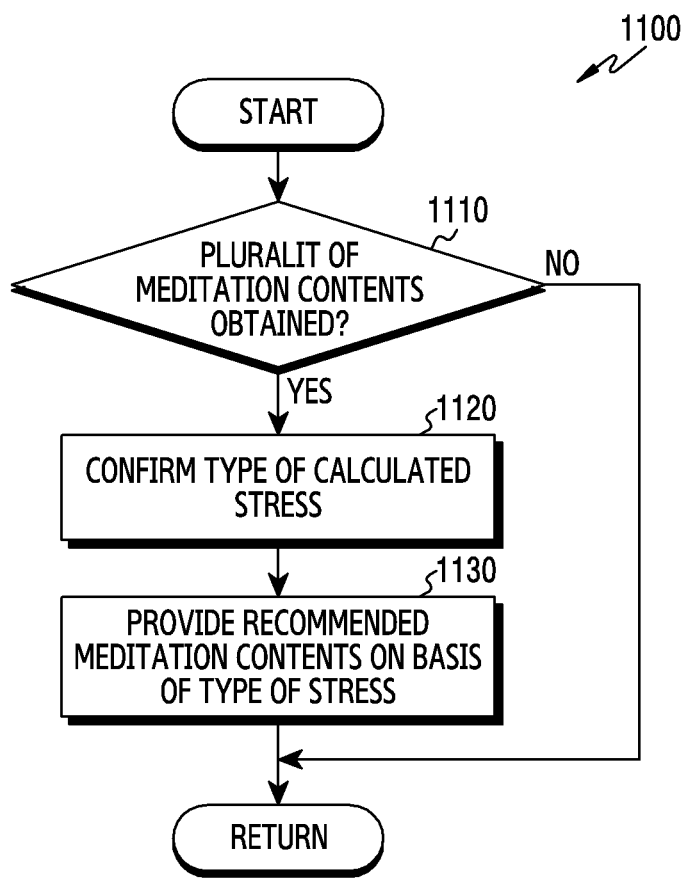
FIG. 11 is a flowchart illustrating an example operation of selecting meditation content in an electronic device according to various embodiments.
Figure 12A:
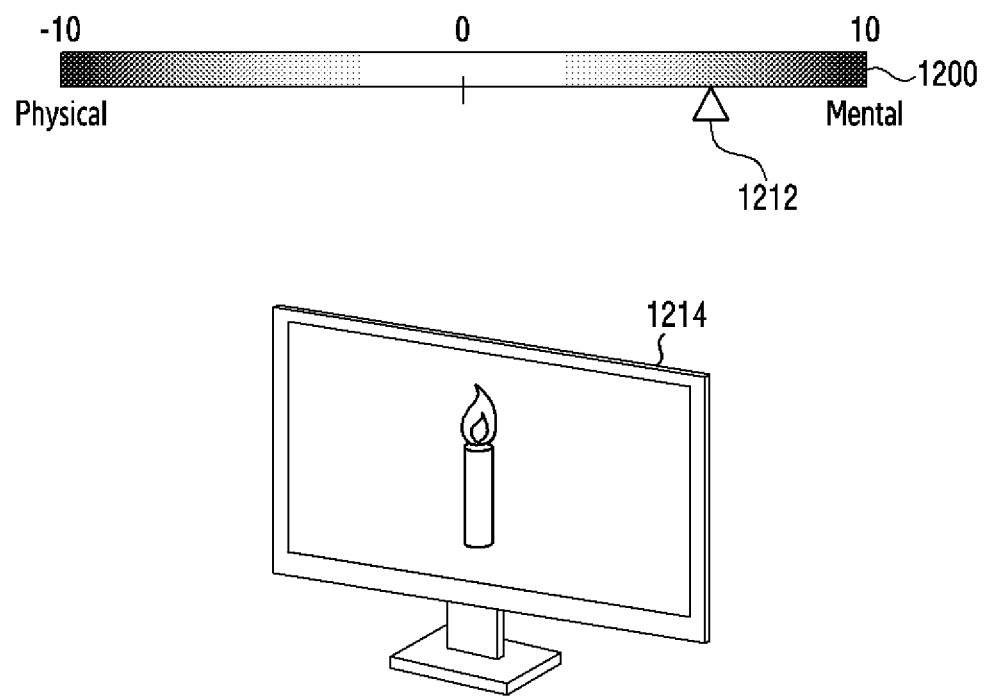
FIGS. 12A and 12B are diagrams illustrating an example situation of recommending meditation contents based on the type of stress.
Figure 12B:
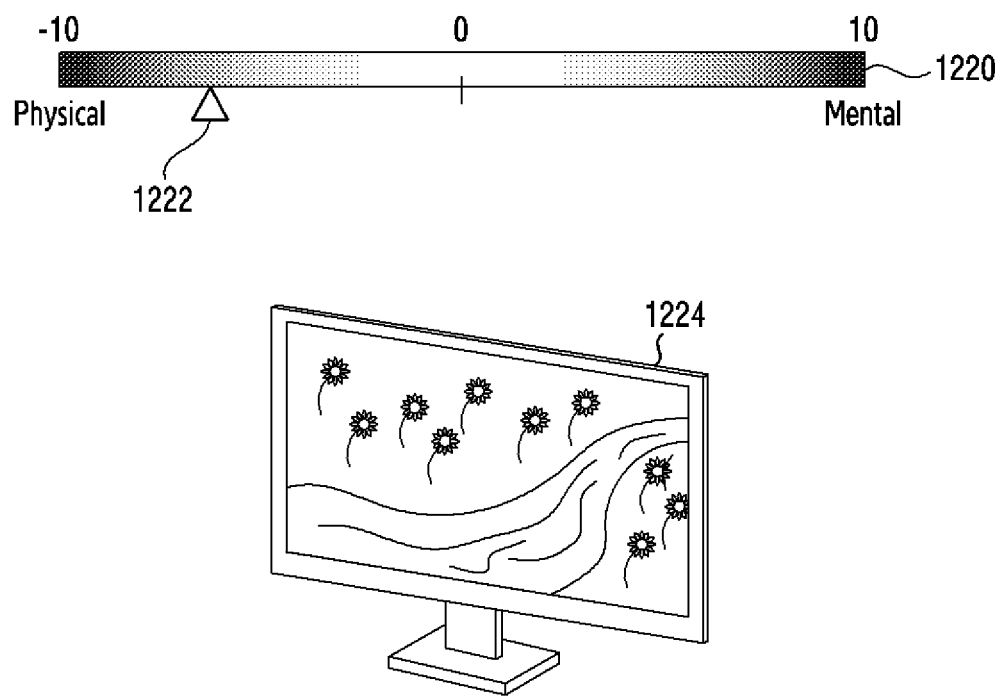

FIG. 11 is a flowchart 1100 illustrating an example operation of selecting meditation content in an electronic device according to various embodiments. FIG. 12A and FIG. 12B are diagrams illustrating an example situation of recommending meditation contents based on the type of stress. Operations of FIG. 11 explained below may be ones representing various embodiments of operation 620 of FIG. 6. Also, in an embodiment below, respective operations may be performed in sequence as well, but are not necessarily performed in sequence. For example, the order of the respective operations may be changed as well, and at least two operations may be performed in parallel as well. The electronic device of FIG. 9 may be the control device 220 of FIG. 3.

Referring to FIG. 11, in operation 1110, the electronic device (e.g., the processor 310 of FIG. 3) of various embodiments may identify whether a plurality of meditation contents (e.g., the meditation contents 411 of FIG. 4) are acquired.

In response to confirming that one meditation content is acquired ("No" in operation 1110), the electronic device (e.g., the processor 310 of FIG. 3) of various embodiments may control the execution of the selected meditation content. For example, the processor 310 may perform an operation related with at least one of operation 630 and operation 640 of FIG. 6.

In response to confirming that the plurality of meditation contents are acquired ("Yes" in operation 1110), in operation 1120, the electronic device (e.g., the processor 310 of FIG. 3) of various embodiments may confirm the type of calculated stress. For example, stress may be divided into mental stress and physical stress.

In operation 1130, the electronic device (e.g., the processor 310 of FIG. 3) of various embodiments may identify recommended meditation contents based on the type of stress. For example, each meditation content may include index information defining stress suitable for relieving through the corresponding meditation content. For instance, as illustrated in FIG. 12A and FIG. 12B, index information 1200 or 1220 may be a criterion for identifying whether the corresponding meditation content is suitable to mental stress or is suitable to physical stress. This index 1200 information may be defined by a meditation contents provider. Also, this index information may be altered based on a use history of meditation contents and stress information of a user who uses the meditation contents as well.

According to an embodiment, the processor 310 may identify recommendation meditation content corresponding to the type of stress using index information of acquired meditation contents. For example, in response to a calculated stress corresponding to mental stress, as illustrated in FIG. 12A, the processor 310 may identify, as recommendation meditation contents, meditation contents (e.g., breathing meditation contents) 1214 including an index 1200 corresponding to a mental stress level 1212 among the acquired meditation contents. For another example, in response to the calculated stress 1222 corresponding to physical stress, as illustrated in FIG. 12B, the processor 310 may identify, as recommendation meditation contents, meditation contents (e.g., sleeping meditation contents) 1224 including an index 1220 corresponding to a physical stress level 1222 among the acquired meditation contents.

According to various example embodiments, an operating method of an electronic device (e.g., the control device 220) may include receiving stress information from at least one collecting device (e.g., the collecting device 210), confirming meditation content corresponding to a stress level based on at least part of the received stress information, confirming at least one executing device (e.g., the executing device 230) related to the confirmed meditation content, and controlling the execution of the confirmed meditation content and the confirmed at least one executing device.

According to various example embodiments, confirming the meditation content may include confirming the meditation content corresponding to the stress level based on at least part of a comparison result of the received stress information and previously stored meta information (e.g., the meta information 410). For example, the meta information may include information matching a stress level to each of a plurality of meditation contents.

According to an example embodiment, confirming the meditation content may include, in response to receiving stress information representing a stress of a first level, identifying first meditation content as the confirmed meditation content, and in response to receiving stress information representing a stress of a second level, identifying second meditation content as the confirmed meditation content.

According to an example embodiment, the meta information may further include at least one of user information, a user state, or environment information. According to an example embodiment, confirming the meditation content may include, in response to receiving supplementary information from the collecting device, confirming the meditation content corresponding to the stress level based on at least part of a comparison result of the received supplementary information and the stored meta information.

According to an example embodiment, controlling the at least one executing device may include controlling an operation of the at least one executing device based on at least part of meta information. For example, the meta information may include information in which a recommended environment is matched to each of a plurality of meditation contents.

According to an example embodiment, controlling the at least one executing device may include, in response to the first meditation content being confirmed, controlling to execute the first meditation content in a first environment, and in response to the second meditation content being confirmed, controlling to execute the second meditation content in a second environment different from the first environment.

According to an example embodiment, the stress information may further include the type of stress. According to an example embodiment, confirming the meditation content may include confirming the meditation content corresponding to the type of stress.

According to an example embodiment, confirming the at least one executing device may include confirming at least one executing device related to the confirmed meditation content among a plurality of executing devices which have been set as a group based on an account of a user.

According to an example embodiment, the operating method of the electronic device may include controlling the collecting device to guide the viewing of the meditation content.

According to an example embodiment, the operating method of the electronic device may include, in response to receiving stress information from the collecting device, identifying that the collecting device enters a previously registered area.

A description has been made for various example embodiments of the present disclosure, but various modifications may be made without departing from the scope of the present disclosure. Therefore, the scope of the disclosure should not be limited and defined to the described embodiment.

What is claimed is:
1. An electronic device comprising:
a communication interface comprising communication circuitry;
a memory; and
at least one processor operatively coupled to the communication interface and the memory, wherein the memory is configured to store instructions that, when executed, cause the processor to control the electronic device to:
receive, using the communication interface, stress-related information relating to a stress level of a user from at least one user-associated collecting sensor device;
identify meditation content corresponding to the stress level of the user and an execution environment for executing the meditation content, based at least in part on the received stress-related information;
identify at least one executing device for executing the identified meditation content and providing the identified execution environment; and
control the least one executing device to execute the identified meditation content and provide the identified execution environment,
wherein control of the at least one executing device is based on receiving, using the communication interface, notification that the at least one collecting device enters a previously registered area;
wherein the previously registered area is a place for playing the meditation content in a recommended environment created by the at least one executing device; and
the processor further configured to control the at least one collecting device, using the communication interface, to provide guide information which guides the user of the at least one collecting device to the previously registered area, based on the at least one collecting device not entering the previously registered area or based on that the at least one collecting device being within a specified proximity to the previously registered area.

2. The electronic device of claim 1, wherein the memory is configured to store meta information associating stress levels to each of a plurality of different meditation contents, and wherein the instructions, when executed, cause the processor to control the electronic device to: identify the meditation content corresponding to the stress level of the user based at least in part on a comparison result of the received stress-related information and the stored meta information.

3. The electronic device of claim 2, wherein the instructions, when executed, cause the processor to control the electronic device to:
based on the received stress-related information representing user stress of a first level, identify first meditation content from among the plurality of meditation content; and
based on the received stress-related information representing user stress of a second level different from the first level, identify second meditation content from among the plurality of meditation contents, the second meditation content being different from the first meditation content.

4. The electronic device of claim 2, wherein the meta information stored in the memory further comprises supplementary information including at least one of user-related information, user state-related information, or environment-related information, and wherein the instructions, when executed, cause the processor to control the electronic device to: based on receiving the supplementary information of the user from the at least one collecting device using the communication interface, identify the meditation content based at least in part on a comparison result of the received stress-related information and the received supplementary information and the stored meta information.

5. The electronic device of claim 1, wherein the memory is configured to store meta information associating stress levels and recommended environments to each of a plurality of different meditation contents, and
wherein the instructions, when executed, cause the processor to identify the at least one executing device based at least in part on a comparison result of the received stress-related information and the meta information.

6. The electronic device of claim 5, wherein the instructions, when executed, cause the processor to:
based on identifying first meditation content according to the received stress-related information, control at least one first executing device to execute the first meditation content and at least one second executing device to provide a first environment in the registered area; and
based on identifying second meditation content according to the received stress-related information, control the at least one first executing device to execute the second meditation content and the at least one second executing device to provide a second environment in the registration registered area different from the first environment.

7. The electronic device of claim 1, wherein the stress-related information further comprises stress-type information, and
wherein the instructions, when executed, cause the processor to control the electronic device to identify meditation content based at least in part on the stress-type information.

8. The electronic device of claim 1, wherein at least two of a plurality of devices, which comprise the electronic device, the at least one collecting device, and the at least one executing device, are the same.

9. The electronic device of claim 1, wherein the at least one executing device comprises:
at least one first executing device for executing the identified meditation content and at least one second executing device different from the at least one first executing device for providing the identified execution environment.

10. A method of operating an electronic device, the method comprising:
receiving, via a communication interface of the electronic device, stress-related information relating to a stress level of a user from at least one user-associated collecting sensor device;
identifying meditation content corresponding to the stress level of the user and an execution environment for executing the meditation content, based at least in part on the received stress-related information;
identifying at least one executing device for executing the identified meditation content and providing the identified execution environment; and
controlling the at least one executing device to execute the meditation content and provide the execution environment,
wherein control of the at least one executing device is based on receiving, using the communication interface, notification that the at least one collecting device enters a previously registered area;
wherein the previously registered area is a place for playing the meditation content in a recommended environment created by the at least one executing device; and controlling the at least one collecting device, via a processor, using the communication interface, to provide guide information which guides the user of the at least one collecting device to the previously registered area, based on the at least one collecting device not entering the previously registered area or based on that the at least one collecting device being within a specified proximity to the previously registered area.

11. The method of claim 10, wherein the step of identifying the meditation content comprises identifying the meditation content corresponding to the stress level of the user based at least in part on a comparison result of the received stress-related information and previously stored meta information, and the meta information comprises information associating stress levels to each of a plurality of different meditation contents.

12. The method of claim 11, wherein the step of identifying the meditation content comprises: based on the received stress-related information representing user stress of a first level, identifying first meditation content from among the plurality of meditation contents; and based on the received stress-related information representing user stress of a second level different from the first level, identifying second meditation content from among the plurality of meditation contents, the second meditation content being different from the first meditation content.

13. The method of claim 11, wherein the meta information further comprises supplementary information including at least one of user-related information, user state-related information, or environment-related information, and
wherein the step of identifying the meditation content comprises, based on receiving the supplementary information of the user from the at least one collecting device, identifying the meditation content based at least in part on a comparison result of the received stress-related information and the received supplementary information and the stored meta information.

14. The method of claim 10, wherein the step of identifying the at least one executing device is based at least in part on a comparison result of the received stress-related information and meta information, and the meta information comprises information associating stress levels and recommended environments to each of a plurality of different meditation contents.

15. The method of claim 14, further comprising: based on identifying first meditation content according to the received stress-related information, controlling at least one first executing device to execute the first meditation content and at least one second executing device to provide a first environment in the registered area; and based on identifying second meditation content according to the received stress-related information controlling the least one first executing device to execute the second meditation content and the at least one second executing device to provide a second environment in the registered area different from the first environment.

16. The method of claim 10, wherein the stress-related information further comprises stress-type information, and the method further comprises: identifying the meditation content based at least in part on the stress-type information.

17. The method of claim 10, wherein at least two of a plurality of devices, which comprise the electronic device, the at least one collecting device and the at least one executing device, are the same.

18. The method of claim 10, wherein the at least one executing device comprises:

at least one first executing device for executing the identified meditation content and at least one second executing device different from the at least one first executing device for providing the identified execution environment.

* * * * *